United States Patent [19]

Yalkowsky

[11] Patent Number: 4,489,026
[45] Date of Patent: Dec. 18, 1984

[54] PROCESS FOR PREPARING SOLID UNIT DOSAGE FORMS OF ULTRA-LOW DOSE DRUGS

[75] Inventor: Samuel H. Yalkowsky, Portage, Mich.

[73] Assignee: The Upjohn Company, Kalamazoo, Mich.

[21] Appl. No.: 415,294

[22] Filed: Sep. 7, 1982

[51] Int. Cl.$^3$ ............................................. A61K 9/00
[52] U.S. Cl. ...................................... 264/123; 427/3; 424/16
[58] Field of Search ............ 427/3, 213; 264/123; 424/16

[56] References Cited

U.S. PATENT DOCUMENTS 3,196,827  7/1965  Wurster ................................ 427/3
3,836,618  9/1974  Stevens ............................... 264/123
3,843,393  10/1974  Groppenbacher .................. 427/213

FOREIGN PATENT DOCUMENTS 544029   5/1952  Canada ................................ 427/213
1133770  11/1968 United Kingdom ................. 427/3

Primary Examiner—Sam Silverberg
Attorney, Agent, or Firm—Flynn, Thiel, Boutell & Tanis

[57] ABSTRACT

A process for the preparation of solid unit dosage forms is disclosed wherein a fine spray of a dilute solution of a pharmaceutically active material is gradually finely sprayed over an extended time period onto fine excipient particles undergoing agitation. Extremely small amounts of the pharmaceutically active material are deposited on the excipient particles, allowing the resulting powder to be formed into solid unit dosage forms, such as tablets, containing 100 mcg or less of the active ingredient per unit, with high content uniformity among the solid unit dosage forms.

7 Claims, No Drawings

PROCESS FOR PREPARING SOLID UNIT DOSAGE FORMS OF ULTRA-LOW DOSE DRUGS

This invention relates to a process for preparing solid unit dosage forms, such as tablets, of pharmaceutical compositions, containing extremely low dosages of pharmaceutically active material. In particular, this invention comprises uniformly spraying small droplets of substantially uniform size of a dilute solution of a pharmaceutically active material onto finely divided, inert, pharmaceutically acceptable, excipient particles, evaporating the solvent to uniformly deposit a large number of very small solid particles of said pharmaceutically active material onto the excipient particles to provide a very low, but highly uniform, concentration of said pharmaceutically active material on said excipient particles, and then forming the excipient particles, having the pharmaceutically active material deposited thereon, into solid unit dosage forms which contain the pharmaceutically active material in substantially uniform amounts of 100 mcg or less, per unit of the solid unit dosage form.

It is sometimes necessary or desired to administer high potency drugs in solid unit dosage forms containing a very small, but pharmacologically effective, amount of the drug. Many of such high potency drugs cannot be formed, by conventional methods, into very small particles of highly uniform size. As a result, it is difficult to provide solid unit dosage forms containing such drugs that will pass the USP Content Uniformity Test, as set forth in United States Pharmacopeia XIX (1975) at page 648. The conventional methods for reducing the particle size of solid drugs include micronizing, milling, and screening processes. These processes, in general, do not produce particles which are sufficiently small and uniform in size for the purposes of the present invention. Another method used to disperse a drug uniformly in excipient particles is granulation. In a granulation process, the drug is dissolved in a solvent and the solution is then added to the excipient particles to form a paste. The thus-formed paste is dried and screened to obtain granules. This type of granulation process is time and energy consuming and may adversely affect the stability of the drug by dissolving material from the excipient particles.

In the following description, the term "coefficient of variation" is defined as being the standard deviation (geometric standard deviation $\delta_g$) of the particles, in percent, divided by the mean (geometric mean diameter $d_g$) of the particles). Thus, a coefficient of variation of 50 percent means that the standard deviation is equal to 50 percent of the mean.

Milling is the most common technique for reducing the particle size of solid drugs. Depending on the type of mill employed and the nature of the drug, milling can produce particle sizes in the range of from 50 and 1,000 microns. However, unless the particles are monodisperse, milling cannot generally be used to prepare particles of solid drugs that are to be administered in dosages of 100 mcg or less, per unit of the solid unit dosage form. Moreover, for a practical operation that provides a relatively uniform distribution of particle sizes having a 50% coefficient of variation and a mean particle size of 100 microns (140 US standard mesh), milling is of marginal effectiveness for preparing particles of solid drugs intended to be administered in dosages below 10 mg per unit of the solid unit dosage form.

In general, the most effective technique for reducing the particle size of a powder of a solid drug is micronization. Micronization, however, is not suitable for all drugs. The frictional heat produced during micronization can cause some drugs to soften or melt and then agglomerate. That heat can also degrade thermally unstable drugs. Even the smallest micronizer consumes up to about 50 grams of the drug in the course of bringing the micronizing machine up to full, steady-state, operating speed. This makes micronization an unacceptable technique for use with drugs that are expensive and/or available in limited quantities.

It is difficult to generalize about either the mean particle size or the particle size distribution produced by micronization. The physical properties of the powder play an extremely important role in determining the extent of its comminution. Particles of 5 to 20 microns in size are commonly produced by micronization. For some materials, particles as small as 1 micron can be obtained, although, for other materials, it is not possible to produce particles of less than 30 microns in size. Size distributions of micronized particles can vary widely with coefficients of variation ranging from 35 to 200%.

If the distribution of the particle sizes obtained is fairly uniform (coefficient of variation less than 50%), and if the mean particle size obtained is below 5 microns, then micronization can be used to produce particles suitable for incorporation into solid unit dosage forms containing dosages of the pharmaceutically active material as low as 1 mcg, per unit of the solid unit dosage form, and such unit dosage forms will pass the Content Uniformity Test. In most cases, however, the mean particle size produced by micronization is greater than 10 microns so that, for example, a tablet containing 1 mcg of the pharmaceutically active material and that will pass the Content Uniformity Test cannot be prepared.

For drugs which cannot be micronized, the minimum dose that can be reliably produced in a single tablet that will pass the Content Uniformity Test can be as much as 1 mg or more.

In order to ensure uniform distribution of potent drugs in solid unit dosage forms that contain very low dosages of the drug, so that said unit dosage forms will pass the Content Uniformity Test, it is necessary to provide the drug in the physical form of extremely fine particles. Forming the drug into extremely fine particles by conventional methods would result in decomposition or melting caused by friction inherent in conventional mechanical methods for producing fine particles.

It is, therefore, an object of the present invention to provide a process for preparing a solid unit dosage form of a pharmaceutical composition containing a small amount of a pharmaceutically active material, wherein the amounts of said pharmaceutically active material in the units of the solid unit dosage form are highly uniform so that the dosage form will pass the Content Uniformity Test.

It is a further object of the invention to provide a process, as aforesaid, for preparing a solid unit dosage form containing dosages of a pharmaceutically active material of 100 mcg or less, per unit of the solid unit dosage form, particularly 10 mcg or less, per unit of the solid unit dosage form.

SUMMARY OF THE INVENTION

To achieve the foregoing objects and purposes of the invention and others related thereto, the invention provides a process for preparing a solid unit dosage form of a pharmaceutical composition wherein the solid unit dosage form contains an ultra low dosage of a pharmaceutically active material. According to the invention, the pharmaceutically active material is dissolved in a volatile solvent to form a very dilute solution of the pharmaceutically active material. This solution is atomized and sprayed, in the form of a fine spray or mist of droplets of substantially uniform size, in a small amount, supplied over an extended period of time, onto fine, inert, pharmacologically acceptable, excipient particles that are undergoing continuous agitation in a surrounding gaseous medium so that the droplets are substantially uniformly deposited on the excipient particles. The excipient particles are insoluble in the solvent. The solvent is continuously slowly evaporated into the surrounding gaseous medium and thereby a large number of very small solid particles of the pharmaceutically active material become deposited uniformly on the excipient particles, without the occurrence of substantial agglomeration of the excipient particles or build-up of significant wetness in the excipient powder. The total weight of the pharmaceutically active material deposited on the excipient particles is very small, but it is in the form of a large number of very small solid particles of substantially uniform size. Upon completion of the spraying and evaporation, the excipient particles having the very small amount of the pharmaceutically active material deposited thereon are formed into individual solid unit dosage forms, such as tablets, each containing a very small, but pharmacologically effective, dosage of the pharmaceutically active material in highly uniform amounts, such that the variation in the amount of the pharmaceutically active material from tablet to tablet is very small, whereby tablets are obtained that pass the Content Uniformity Test.

DETAILED DESCRIPTION

The present invention provides a process for preparing solid unit dosage forms containing 100 micrograms or less, preferably 10 micrograms or less, of the pharmaceutically active material per each unit of the solid unit dosage form, wherein the solid unit dosage form passes the Content Uniformity Test. According to the present invention, fine droplets of substantially uniform size of a dilute solution of the drug are sprayed onto the excipient powder and then the solvent is evaporated so that a large number of very small particles of the drug, which particles are of highly uniform size, are incorporated in the excipient powder. Solid unit dosage forms made of the thus-treated excipient powder exhibit high uniformity of the content of the drug from one dosage unit to another.

In a preferred embodiment of the process of the invention, the pharmaceutically active material is dissolved in an inert liquid solvent at a concentration in the range of from about 0.01 to 10 micrograms of the pharmaceutically active material per one milliliter of the solvent. The resulting solution is then atomized and sprayed, in a form of a fine spray or mist of droplets of substantially uniform size, from a spraying nozzle, spinning disk or other suitable atomizing and spraying apparatus, onto the excipient powder. While the solution of the drug is being sprayed onto the excipient powder, the excipient powder is subjected to agitation, for example in an inclined rotating tumbler pan of the type conventionally used for coating pharmaceutical tablets, to ensure even distribution of the drug solution on the excipient particles. Although the use of a tumbler pan is preferred for this step, this step can also be carried out using a fluidized bed or spouted bed apparatus wherein the excipient particles are suspended in a flowing gas stream. U.S. Pat. No. 3,903,839 illustrates a machine of this type.

The drug solution is preferably atomized and sprayed onto the agitated excipient powder at a relatively slow volumetric rate so that wetness does not build up in the excipient powder and said excipient powder remains in a substantially dry, free-flowing state. For example, the solution can be sprayed at a rate of 1 to 10 ml/min. over a period of about 10 to 30 minutes. The total spraying time should be preferably at least about 10 minutes in order to avoid wetness build-up in the excipient powder which might lead to undesirable agglomeration. The upper limit of the total spraying time is not critical, but a maximum period of about 30 minutes is preferred from an economic point of view. The simultaneous atomizing, spraying and tumbling step is normally carried out in the absence of externally supplied heat that might melt or decompose the pharmaceutically active material. However, if the pharmaceutically active material is heat tolerant, then heating at a low temperature can be done to speed up the process. During the spraying and tumbling step, a suitable gas, such as air or, if necessary or desirable, an inert gas, is circulated over the tumbling particles to facilitate evaporation of the solvent. The gas may be warmed to speed up evaporation of the solvent, if desired.

The inert powder used as the excipient powder in the present invention can be any pharmacologically acceptable excipient, or mixture thereof, that is compatible with the pharmaceutically active material. The excipient should be insoluble in the solvent. The use of highly absorbent substances, such as kaolin and bentonite, as the excipient should be avoided if the pharmaceutically active material would be absorbed therein to such a degree that it would not be completely available after administration. For example, lactose, starch, calcium carbonate, titanium dioxide, silicon dioxide, dicalcium phosphate, microcrystalline cellulose, sodium alginate, calcium sulfate, talc, or any similar GRAS-listed powder are suitable for use as the excipient powder in the present invention. The excipient is used in the form of a fine powder having a particle size within the range conventionally used in the preparation of solid unit dosage forms, such as tablets and capsules. The excipient powder preferably possesses good flow and compressibility characteristics and is sufficiently cohesive to act as a binder so that it is suitable as a direct compression vehicle or carrier capable of being formed into tablets by the well-known direct compression method for making compressed tablets containing drugs. Thus, the excipient particles containing the pharmaceutically active material incorporated therein, according to the invention, can be compressed to form tablets directly without granulation or other modification of the physical nature of powdered material itself. No colloidal binders, such as gelatin or starch, are required.

The liquid solvent is selected so that the pharmaceutically active material is soluble therein in the low concentrations required. The pharmaceutically active material must be compatible with and stable in the solvent. The liquid solvent is a nonsolvent for the excipient powder. Also, the solvent is sufficiently volatile that it will be readily evaporated during the tumbling process in the presence of air or other gaseous medium. Nonaqueous organic solvents having boiling points lower than 80° C. are particularly preferred because a wider variety of pharmaceutically active materials are more readily soluble therein than in an aqueous solvent. Preferred solvents include methylene chloride, ethyl acetate, ethanol, methanol, and fluorinated hydrocarbon (Freon) compounds and mixtures of the above.

The pharmaceutically active material can be any such material which is to be administered in a dosage, per unit of the solid unit dosage form, of less than 100 mcg. The process of the invention is especially effective for preparing solid unit dosage forms of pharmaceutically active materials that must be administered in extremely small dosages of less than 10 mcg per unit of the solid unit dosage form. Examples of known drugs advantageous for use in the present invention include various prostaglandins, oxytocin and other peptides, vasopressin, vitamin B-12, VIP analog, LHRH analogs, and the like.

The solution of the pharmaceutically active material is atomized and sprayed and is thereby deposited in the form of small liquid droplets of substantially uniform size on the excipient powder. The solvent is then evaporated from the liquid droplets so that the pharmaceutically active material forms a very large number of very small dry solid particles deposited on or in close association with the excipient powder particles. The weight of each particle of the pharmaceutically active material will depend on the volume of the droplet from which it was derived and the concentration of the pharmaceutically active material in that droplet. Thus, the type of spray nozzle or spinning disk used will be selected, taking into consideration the concentration of the pharmaceutically active material in the solution, so that the droplets it produces will provide the requisite large number of very small dry solid particles of the pharmaceutically active material on the excipient powder. Suitable nozzles for spraying droplets of substantially uniform size are well-known and they can be used in this invention. For example, satisfactory nozzles include Spraying Systems E15 Nordson 000-02, 000-04 and 000-06. Because the concentration of the pharmaceutically active material in the solution can vary over a wide range, the droplet size to be generated by the spraying nozzle can similarly vary, that is, when a dilute solution is sprayed, the droplet size can be larger whereas when a more concentrated solution is sprayed, the droplet size will be smaller. After the atomizing, spraying and evaporation steps are completed, the pharmaceutically active material is present as a very large number of very small particles which are uniformly distributed in very small amounts on the excipient particles. The excipient particles are then taken and formed by conventional methods into solid unit dosage forms, such as tablets or capsules, or the drug can be administered in powder form.

Typical proportions for the process of the invention are as follows. To make 1,000 tablets each containing one microgram of the pharmaceutically active material and 200 milligrams of excipient, 200 grams of a fine excipient powder are first placed in a rotating coating pan. 1 milligram of the pharmaceutically active material is dissolved in 30 milliliters of the solvent. The solution is atomized and sprayed finely and slowly, over a period of 15 minutes, as described above onto the tumbling powder. Additional excipient may be added during the tumbling process as necessary.

The process of the invention is successful in producing solid unit dosage forms, such as tablets, of high uniformity and containing a low dosage level of the pharmaceutically active material. The process of the present invention is distinctly superior to the prior art micronization and milling processes in these respects. Solid unit dosage forms according to the invention comprise a multiplicity of very small particles of the pharmaceutically active material which have a more uniform size distribution than comparable particles produced by the micronization or milling methods. The process of the invention is therefore suitable for manufacturing solid unit dosage forms in which the content of the pharmaceutically active material, per unit of solid unit dosage form, is sufficiently uniform to pass the USP Content Uniformity Test even though the dosage is very small. The requirements of the USP Content Uniformity Test referred to above are as follows.

"The requirements are met if the content of each of 10 tablets is within the limits of 85.0 percent and 115.0 percent of the average of the limits specified in the potency definition in the individual monograph".

"If the content of not more than one tablet falls outside the limits of 85.0 percent and 115.0 percent and if the content of none of the tablets falls outside limits of 75.0 percent and 125.0 percent of that average, assay each of the remaining 20 tablets. The requirements are met if the content of each of the additional 20 tablets falls within the limits of 85.0 percent and 115.0 percent of the average of the limits specified in the potency definition in the individual monograph unless otherwise stated in the individual monograph."

The above requirements for tablets are intended to ensure that the active ingredient is distributed substantially uniformly among the individual units of a batch.

The process of the invention is effective consistently to produce particles of the pharmaceutically active material having a maximum mean particle diameter in the range of from about 0.5 to about 10 microns, depending on the concentration of the solution of said pharmaceutically active material and the droplet size thereof that is sprayed onto the excipient particles. Because of variations in the performance of the spraying step, in any single given batch process, the coefficient of variation of the particle diameters of the pharmaceutically active material, measured by the Log Normal Distribution Curve, is not precisely controllable and is variable up to about 100%. However, by providing a solid unit dosage form in which the pharmaceutically active material is present in the form of a very large number of very small particles having the selected maximum mean particle diameter, the probability that the total weight of the drug in a given tablet will be outside the limits of the Content Uniformity Test, because of variations of the individual particle sizes of the pharmaceutically active material, will be at such a low level (less than 1%) that it can be expected that the tablets will pass the USP Content Uniformity Test.

The embodiments of the invention in which an exclusive property or privilege is claimed are defined as follows:

1. A process for the preparation of a solid unit dosage form, pharmaceutical composition containing an ultra-low dosage of a pharmaceutically active material, comprising the steps of:

dissolving said pharmaceutically active material in a volatile inert solvent to form a dilute solution of said pharmaceutically active material;

atomizing and uniformly spraying said solution in the form of fine droplets, in a small amount, over an extended time period, onto fine, inert, pharmacologically acceptable, excipient particles which are undergoing continuous agitation while in contact with surrounding gaseous medium, said excipient particles being insoluble in said solvent, and continuously evaporating said solvent and depositing large numbers of very small solid particles of said pharmaceutically active material uniformly on said excipient particles under conditions effective to prevent substantial agglomeration of said excipient particles or build-up of wetness in said excipient particles; and then forming said excipient particles containing said particles of said pharmaceutically active material into said solid unit dosage form pharmaceutical composition having an effective dosage of not more than 100 micrograms of said pharmaceutically active material per unit of said solid unit dosage form.

2. A process according to claim 1, wherein said solvent is a nonaqueous solvent having a boiling point lower than 80° C.

3. A process according to claim 1, wherein said pharmaceutically active material is dissolved in said solvent at a concentration of not greater than 10 mcg/ml, and said solution is sprayed onto said excipient particles at a rate of 1 to 10 ml/min, over a period of at least approximately ten minutes.

4. A process according to claim 1, claim 2 or claim 3, wherein said solid unit dosage form pharmaceutical composition has an effective dosage of said pharmaceutically active material of not more than 10 mcg per unit of said solid unit dosage form.

5. A process according to claim 1, claim 2 or claim 3, wherein said solvent is selected from the group consisting of methylene chloride, ethyl acetate, ethanol, methanol, fluorinated hydrocarbon compounds and mixtures thereof.

6. A process for the preparation of pharmaceutical tablets containing an ultra-low dosage of a pharmaceutically active material, which material is present as extremely fine particles in the tablets, comprising the steps of:

dissolving said pharmaceutically active material in an inert, volatile, non-aqueous, organic solvent having a boiling point of less than 80° C. to form a solution containing from about 0.01 to about 10 micrograms of said pharmaceutically active material per milliliter of said solvent;

atomizing and uniformly spraying said solution, in the form of fine droplets, at a rate of from about 1 to about 10 milliliters per minute, for a time period of from about 10 to about 30 minutes, onto fine, inert, pharmacologically acceptable, excipient particles which are insoluble in said solvent, are disposed in a rotating, inclined, tumbler pan and are undergoing continuous tumbling therein while in contact with a surrounding gaseous medium so that said droplets are substantially uniformly deposited on said excipient particles, and continuously slowly evaporating said solvent into said surrounding gaseous medium and thereby depositing a large number of very small solid particles of said pharmaceutically active material on said excipient particles, said particles of said pharmaceutically active material being of highly uniform size and having a maximum mean particle diameter in the range of from about 0.5 to about 10 microns whereby to provide a very low, highly uniform concentration of said pharmaceutically active material on said excipient particles, the atomizing and spraying steps being carried out under conditions effective to prevent substantial agglomeration of said excipient particles and build-up of wetness in said excipient particles; and then forming said excipient particles containing said particles of said pharmaceutically active material into tablets by the direct compression method, each of said tablets containing not more than 100 micrograms of said pharmaceutically active material.

7. A process according to claim 6 in which said step of forming tablets is performed by placing a charge consisting essentially of said excipient particles containing said particles of said pharmaceutically active material into a die cavity, compressing said charge in said cavity between two punches to form the same into a tablet by the direct compression method effective for forming pharmaceutical tablets, and ejecting said tablet from said die cavity.

* * * * *